United States Patent [19]

Sugiura et al.

[11] Patent Number: 5,602,103
[45] Date of Patent: Feb. 11, 1997

[54] CEREBRAL FUNCTION-AMELIORATING AGENT

[75] Inventors: Minoru Sugiura, Takahagi; Hiroshi Saito, Tokyo; Yukihiro Syoyama, Kasuga, all of Japan

[73] Assignee: Nippon Mektron, Limited, Tokyo, Japan

[21] Appl. No.: 398,238

[22] Filed: Mar. 3, 1995

[51] Int. Cl.$^6$ ............................ A61K 31/70; C07H 3/00
[52] U.S. Cl. ...................... 514/25; 514/53; 536/4.1; 536/115
[58] Field of Search ................ 536/4.1, 115; 514/25, 514/53

[56] References Cited

U.S. PATENT DOCUMENTS

| | | | |
|---|---|---|---|
| 3,922,368 | 11/1975 | Klaui et al. | 426/540 |
| 5,424,407 | 6/1995 | Tanaka et al. | 536/4.1 |

OTHER PUBLICATIONS

Nippon Yakugakkai, Society of Pharmaceutical Sciences of Japan, No. 133 Annual Conference Lecture Summary, p. 35.

*Primary Examiner*—Elli Peselev
*Attorney, Agent, or Firm*—Barnes & Thornburg

[57] ABSTRACT

Crocetin disaccharide esters represented by the following general formula:

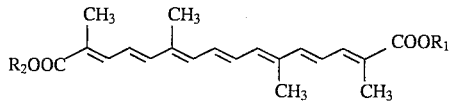

wherein $R_1$ and $R_2$ are gentiobiose groups or glucose groups and may be the same or different groups from each other, are effective for dose-dependently improving the hippocampal long-term potentiation blocking effect of ethanol and are used as an effective cerebral function-ameliorating agent.

3 Claims, 3 Drawing Sheets

CEREBRAL FUNCTION-AMELIORATING AGENT

BACKGROUND OF THE INVENTION

1. Field of the Invention

The present invention relates to a cerebral function-ameliorating agent and more particularly to a cerebral function-ameliorating agent without any substantial fear for side effects.

2. Description of the Prior Art

With recent increasing population of aged persons, there are more and more people suffering from cerebral functional disorders such as cerebral blocking, dementia, etc. Various synthetic medicaments have been clinically offered to these symptoms as cerebral circulation-metabolism ameliorating medicaments, but in the current actual situation various side effects caused by long term dosage due to properties specific to these medicaments have been unavoidable.

As a result of studies on effects of alcohol extract of *Crocus sativus L.* on memory and learning, the present inventors found that it was effective for the learning behavior of mice in passive avoidance tasks [Nippon Yakugakkai (Society of Pharmaceutical Sciences of Japan), No.133 Annual Conference Lecture Summary, page 35].

SUMMARY OF THE INVENTION

An object of the present invention is to provide a cerebral function-ameliorating agent without any substantial fear for side effects, which is a carotenoid derivative isolated from *Crocus sativus L.*, etc.

According to the present invention, there is provided a cerebral function-ameliorating agent, which comprises a crocetin disaccharide ester, represented by the following general formula:

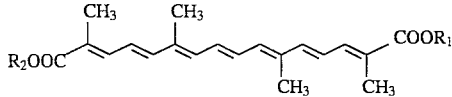

wherein $R_1$ and $R_2$ are gentiobiose groups or glucose groups and may be the same or different groups from each other.

DETAILED DESCRIPTION OF THE INVENTION

Crocetin (8,8'-diapocarotenedioic acid, which is a compound with $R_1$ and $R_2$ each being a hydrogen atom in the above-mentioned formula) is a carotenoid compound (red crystal) isolated from *Crocus sativus L.*. In the present invention, digentiobiose ester [crocin], monoglucose monogentiobiose ester or diglucose ester thereof is used as an effective component of the present cerbral function-ameliorating agent, where the esterified gentiobiose is a reducible disaccharide whose two D-glucose molecules are combined together at $\beta 1-6$.

That is, crocetin is one of several hundred carotenoid pigments contained in plants, and these carotenoid pigments have been actually used as medicaments ($\beta$-carotin, etc.), food-coloring agents, antioxidants, etc. and can be deemed to be compounds without any substantial fear for side effects.

The above-mentioned compounds are available in the form of medicaments or foodstuff. In case of medicaments, they are offered in the form of powder, granules, tablets, sugar-coated tablets, capsules, liquids, etc. In case of foodstuff, they are offered in the form of gum, candy, zelly, tableted cake, beverage, etc. In case of medicaments, they can be administered perorally, parenterally, by inhalation, by perrectum, locally, etc. Parenteral administration includes, for example, subcutaneous, intracerebral-lateraventicular, intravenous, intramuscular, intranasal administrations or injections, etc. Administration dose is generally in a range of about 10 to 500 mg/kg body weight for one administration, and usually 1 to 5 administrations are made daily. Exact dose is selected from the above-mentioned range in view of age, body weight and symptom of a patient, administration route, etc.

Their toxicity is low and investigation of their acute toxicity on male Wistar rats by oral administration showed no killing cases even at a dose as much as 3,000 mg/kg (p.o.).

It is known that ethanol induces a memory deficit to animals. As a result of studies of these crocetin disaccharide esters on hippocampal long-term potentiation, which is deemed to be closely related to memory and learning, the present inventors have found that these medicaments are effective for dose-dependently improving the hippocampal long-term potentiation blocking effect of ethanol and thus effective as a cerebral function-ameliorating agent.

PREFERRED EMBODIMENTS OF THE INVENTION

Example

1) Effects of Medicaments on Rats Hippocampal Long-term Potentiation

Male Wister rats, 8 to 9 weeks old, were anesthetized with urethan-chloralose and an intravenous administration canule was inserted into the rear foot vein and fixed to a cerebral stereotaxic apparatus. Impulses of 0.8 m sec duration were given to the medial perforant path at intervals of 30 seconds and evoked potentials from the granule cell layer of hippocampal dentate gyrus were extracellularly recorded. Stimulus intensity was set to a level which produced a population spike of about 50% of the maximum amplitude. After the evoked potentials became stable, medicaments were administered.

Hippocampal long-term potentiation could be induced only by one application of strong tetanic stimulation of 30 pulses at 60 Hz to the medial perforant path. After the application of strong tetanic stimulation, evoked potentials were recorded for 60 minutes to calculate potentiation percentages to the evoked potential before the application of strong tetanic stimulation.

2) Long-term Potentiation Blocking Effect of Intravenously Administered 30% Ethanol and Effects of the Medicaments According to the Present Invention 20 minutes before the application of tetanic stimulation, the following medicaments 1 to 3 of the present invention, which were each isolated from the pistils of *Crocus sativus L.* as extracts, were intracerebroventricularly administered, and 5 minutes thereafter 30% ethanol was administered at a dose of 2 ml/kg.

Medicament 1: Crocetin digentiobiose ester
(Administration dose: 51.2 n mol)
Medicament 2: Crocetin monogentiobiose monoglycose ester
(Administration dose: 102.4 n mol)
Medicament 3: Crocetin diglucose ester
(Administration dose: 102.4 n mol)

Figure 3:
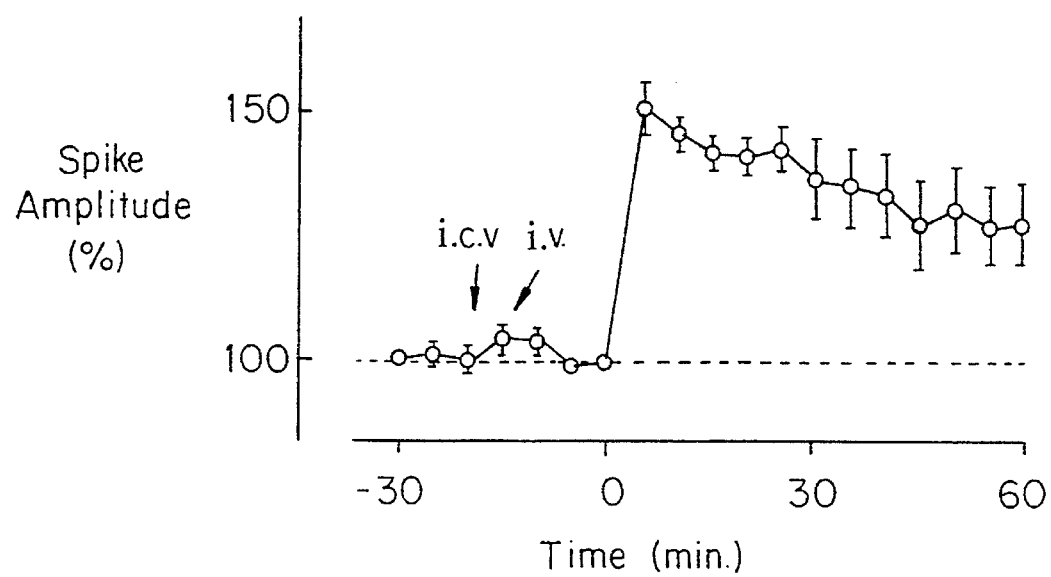
FIG. 3 is a diagram showing an effect of medicament 1 on the long-term potentiation blocking effect of intravenously administered ethanol.
Figure 4:
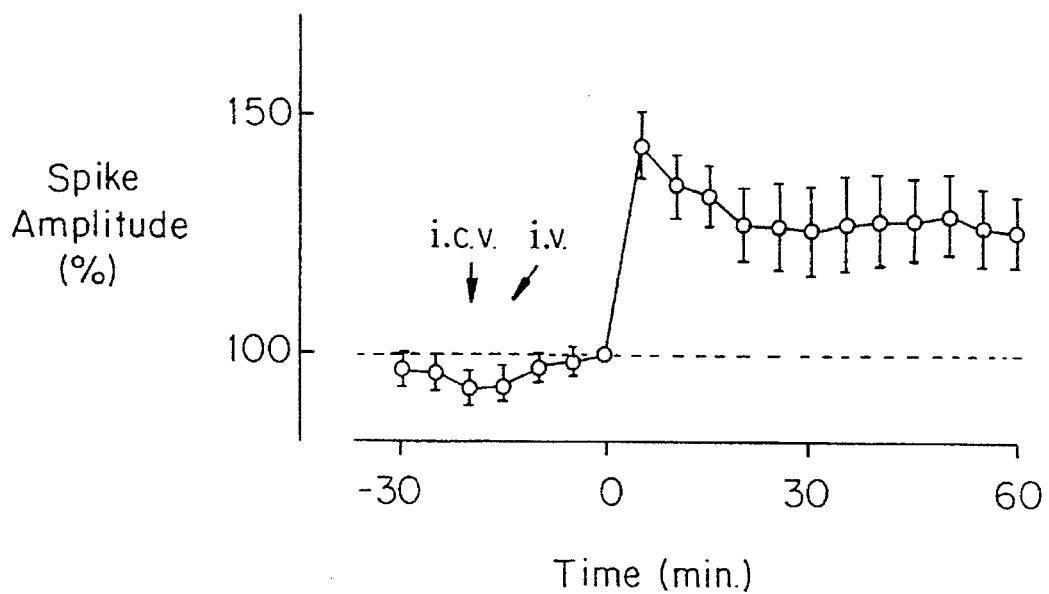
FIG. 4 is a diagram showing an effect of medicament 2 on the long-term potentiation blocking effect of intravenously administered ethanol.
Figure 5:
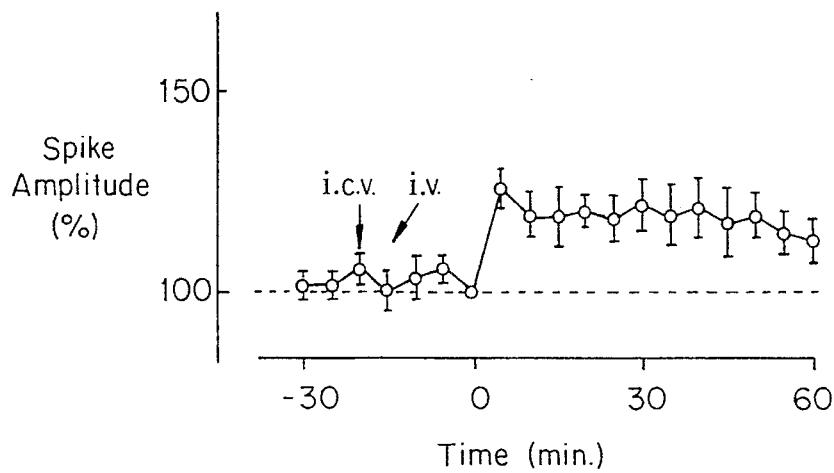
FIG. 5 is a diagram showing an effect of medicament 3 on the long-term potentiation blocking effect of intravenously administered ethanol.

Effects of the respective medicaments on the long-term potentiation blocking effect of intravenously administered ethanol were determined as spike amplitude and compared several data sets of time course curve of potentiation. Results are shown in FIGS. 3 to 5.

Figure 1:
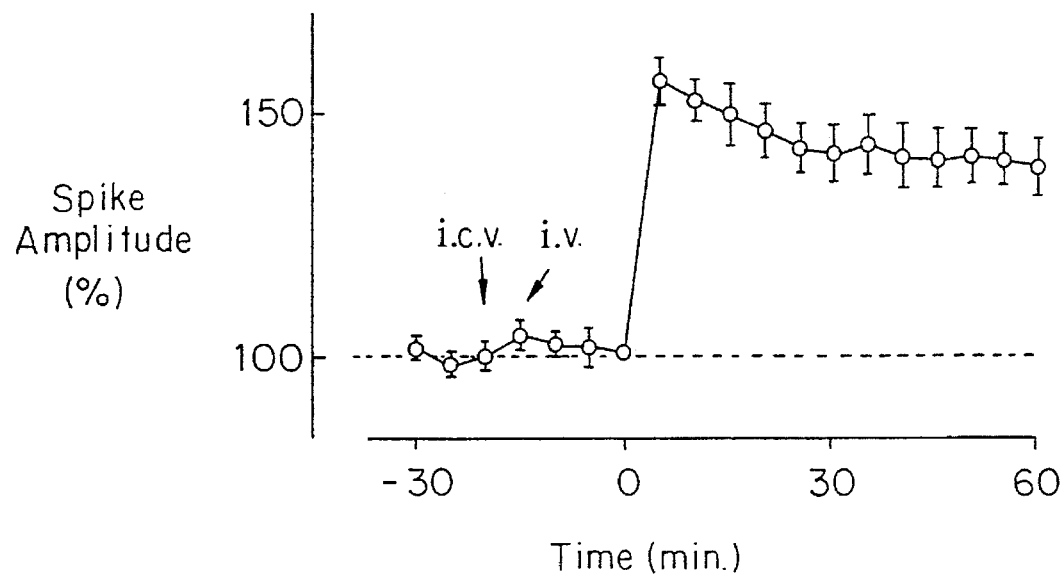
FIG. 1 is a diagram showing evoked long-term potentiation in control group.

FIG. 1 is a diagram showing evoked long-term potentiation of intracerebroventricular administration of 5 μl of physiological saline and intravenous administration of physiological saline at 2 ml/kg in the control group as time course curves of spike amplitude (potentiation percentages of evoked potentials).

Figure 2:
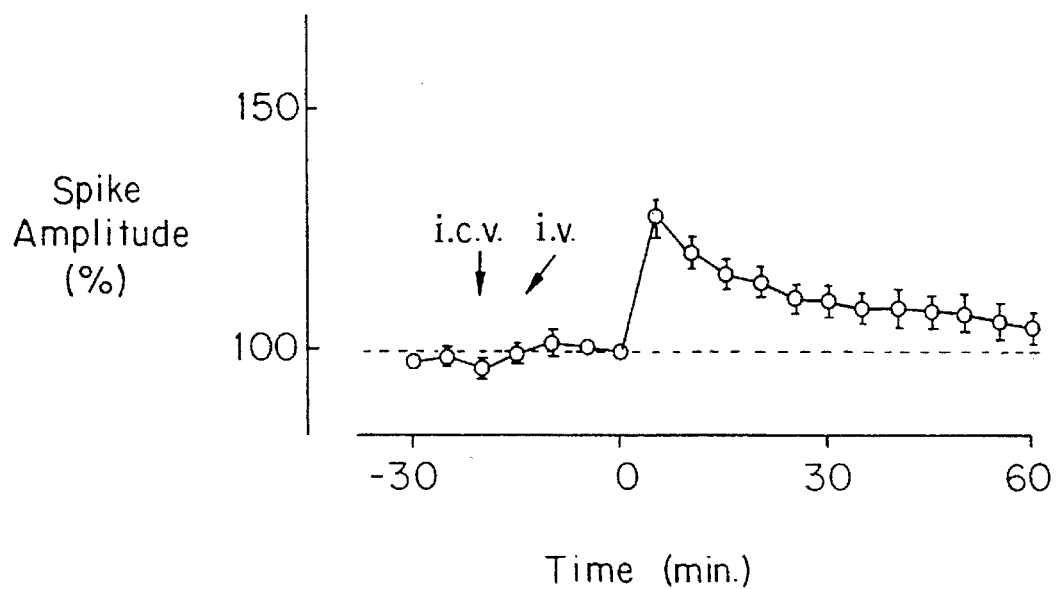
FIG. 2 is a diagram showing long-term potentiation blocking effect of intravenously administered ethanol.

FIG. 2 is a diagram showing long-term potentiation blocking effect of intracerebroventricular administration of 5 μl of physiological saline and intravenous administration of 30% ethanol at 2 ml/kg as time course curve of spike amplitude (potentiation percentages of evoked potentials), where i.c.v. means intracerebroventricular administration and i.v. means intravenous administration.

After the application of tetanic stimulation, area under curve (AUC) was integrally calculated for a duration of 5 min. to 60 min. to dermine a significant difference according to Duncan's multiple range test, where symbols have the following meanings:

\*\* $P<0.01$ vs. control group (n=6)
\# $P<0.05$
\#\# $P<0.01$ vs. 30% ethanol alone (n=13)

Figure 6:
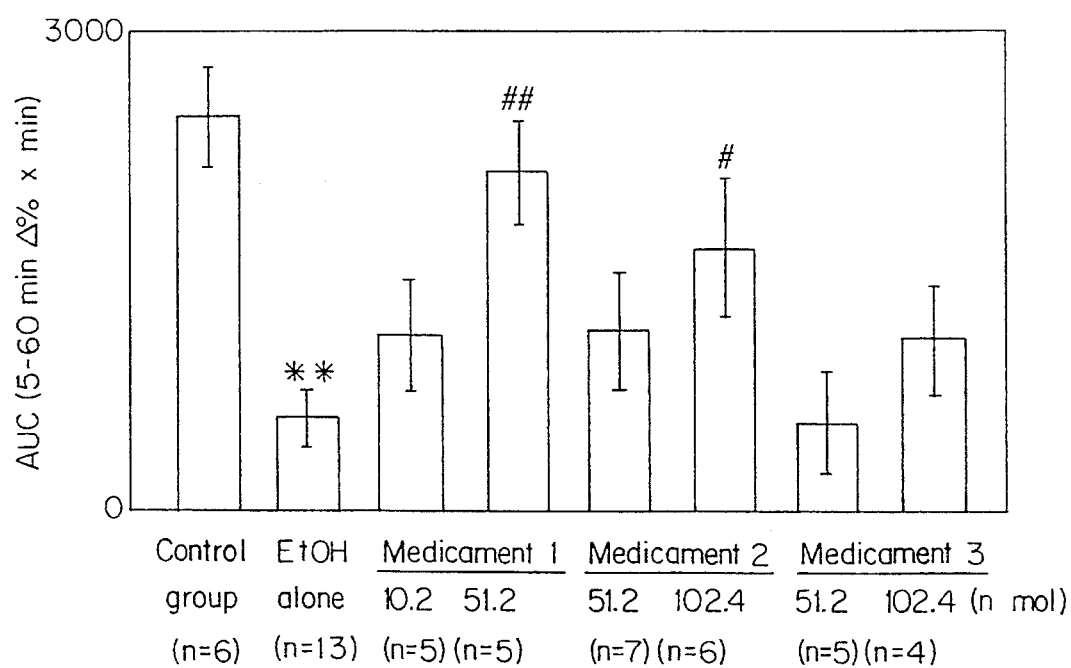
FIG. 6 is a diagram showing the effects of medicaments 1 to 3 on the long-term potentiation blocking effect of intravenously administered ethanol calculating area under curve.

Medicaments 1 to 3 were intracerebroventricularly administered at the above-mentioned administration doses and 5 minutes thereafter 30% ethanol was intravenously administered at 2 ml/kg. In the diagram of FIG. 6, the intracerebroventricularly administered medicaments and their administration doses (unit: n mol) are shown on the abscissa.

What is claimed is:

1. An ameliorating compound for treating memory deficit induced by ethanol which has the formula:

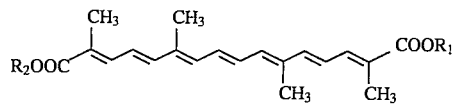

wherein $R_1$ and $R_2$ are gentiobiose groups or glucose groups and are the same or different from each other.

2. A method of treating memory deficit induced by ethanol which comprises administering to a subject experiencing a memory deficit induced by ethanol an effective amount of an ameliorating compound which has the formula:

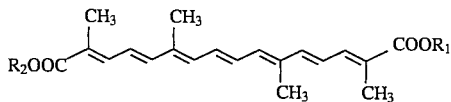

wherein $R_1$ and $R_2$ are gentiobiose groups or glucose groups and are the same or different from each other.

3. A method of treating memory deficit induced by ethanol according to claim 2, wherein said effective amount is in the range of from about 10 mg/kg body weight of said subject to about 500 mg/kg body weight of said subject.

\* \* \* \* \*